United States Patent
Gorochow (10) Patent No.: US 10,292,851 B2
(45) Date of Patent: May 21, 2019

(54) SELF-EXPANDING DEVICE DELIVERY APPARATUS WITH DUAL FUNCTION BUMP

(71) Applicant: DePuy Synthes Products, Inc., Raynham, MA (US)

(72) Inventor: Lacey Gorochow, Miami, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 46 days.

(21) Appl. No.: 15/281,974

(22) Filed: Sep. 30, 2016

(65) Prior Publication Data

US 2018/0092766 A1 Apr. 5, 2018

(51) Int. Cl.
| | |
|---|---|
| *A61F 2/966* | (2013.01) |
| *A61F 2/844* | (2013.01) |
| *A61F 2/86* | (2013.01) |
| *A61F 2/95* | (2013.01) |

(52) U.S. Cl.
CPC .............. *A61F 2/966* (2013.01); *A61F 2/844* (2013.01); *A61F 2/86* (2013.01); *A61F 2002/9534* (2013.01); *A61F 2002/9665* (2013.01); *A61F 2210/0014* (2013.01)

(58) Field of Classification Search
CPC ................................ A61F 2/966; A61F 2/844
See application file for complete search history.

(56) References Cited

U.S. PATENT DOCUMENTS

| | | |
|---|---|---|
| 5,702,418 A | 12/1997 | Ravenscroft |
| 6,123,723 A | 9/2000 | Konya et al. |
| 6,264,683 B1 | 7/2001 | Stack et al. |
| 6,280,465 B1 | 8/2001 | Cryer |
| 6,612,012 B2 | 9/2003 | Mitelberg et al. |
| 6,673,106 B2 | 1/2004 | Mitelberg et al. |
| 6,818,013 B2 | 11/2004 | Mitelberg et al. |

(Continued)

FOREIGN PATENT DOCUMENTS

| | | |
|---|---|---|
| EP | 2777638 A1 | 9/2014 |
| EP | 2777649 A1 | 9/2014 |

(Continued)

OTHER PUBLICATIONS

Partial European Search Report dated Feb. 13, 2018 during the prosecution of European Patent Application 17194063.8.

*Primary Examiner* — Richard G Louis (74) *Attorney, Agent, or Firm* — Troutman Sanders LLP (57) ABSTRACT

A self-expanding element delivery apparatus includes a catheter having an inner lumen, a self-expanding element, and a delivery wire disposed within and extending through the inner lumen and the self-expanding element. The self-expanding element has a proximal, distal, and an intermediate portion. The element has anchor members, a compressed configuration fitting within the inner lumen, and an expanded configuration dimensioned larger than the catheter. The delivery wire also has proximal and distal portions, an intermediate portion, a dual function bump member disposed approximate to the intermediate portion, and a pusher bump member disposed approximate to the proximal portion of the delivery wire. A bump member distance between the dual function bump member and the pusher bump member is such that so that only one of the dual function bump member and the pusher bump member can contact one of the anchor members.

2 Claims, 6 Drawing Sheets

(56) References Cited

U.S. PATENT DOCUMENTS

| | | |
|---|---|---|
| 6,833,003 B2 | 12/2004 | Jones et al. |
| 6,955,685 B2 | 10/2005 | Escamilla et al. |
| 6,960,227 B2 | 11/2005 | Jones et al. |
| 6,960,228 B2 | 11/2005 | Mitelberg et al. |
| 7,001,422 B2 | 2/2006 | Escamilla et al. |
| 7,037,331 B2 | 5/2006 | Mitelberg et al. |
| 7,201,769 B2 | 4/2007 | Jones et al. |
| 7,309,351 B2 | 12/2007 | Escamilla et al. |
| 8,092,510 B2 | 1/2012 | Metcalf et al. |
| 8,597,276 B2 | 12/2013 | Vongphakdy et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,775,706 B2 | 3/2017 | Peterson et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 2005/0049668 A1 | 3/2005 | Jones et al. |
| 2005/0049669 A1 | 3/2005 | Jones et al. |
| 2011/0307049 A1 | 12/2011 | Kao |
| 2014/0277360 A1* | 9/2014 | Girnary ............... A61F 2/848 |
| | | 623/1.12 |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |

FOREIGN PATENT DOCUMENTS

| | | |
|---|---|---|
| WO | 9943379 A1 | 9/1999 |
| WO | 2013126299 A1 | 8/2013 |

* cited by examiner

SELF-EXPANDING DEVICE DELIVERY APPARATUS WITH DUAL FUNCTION BUMP

FIELD OF THE INVENTION

This invention relates generally to devices for interventional therapeutic treatment or vascular surgery for treatment of defects in the vasculature, and more particularly concerns a system for delivering a self-expanding device or stent to a treatment site in a body lumen of a patient.

BACKGROUND

Cardiac stents, which are an example of a self-expanding device, are inserted into a blood vessel to provide an open path within the blood vessel, have been widely used in intravascular angioplasty treatment of occluded cardiac arteries, and in other applications. Stents are often deployed by use of inflatable balloons, or mechanical devices which force the stent open, thereby reinforcing the artery wall and provide a clear through-path in the center of the artery after the angioplasty procedure to prevent restenosis. The use of placement techniques, such as balloons or mechanical expansions of the type often found to be useful in cardiac surgery, are relatively less useful in vasoocclusive surgery, particularly when tiny vessels, such as those found in the brain, are to be treated.

Other stents are self expanding and are just deployed inside of the vascular. Their self-expanding nature allows them to be smaller as well as the devices to deploy them. There are different techniques to deploy the stents, and each has benefits and drawbacks. One expandable stent and delivery system is known that includes an expandable stent having proximal and distal anchor members mounted on proximal and distal legs extending proximally and distally from the stent. The proximal and distal anchor members of the expandable stent are mounted in gaps formed between proximal, intermediate and distal cylindrical members disposed on and spaced apart along an elongated core member. However, pushing the device distally in a catheter from the proximal end of the device is not optimal, because application of force in a distal direction on the proximal end of the stent can axially compress the stent, and can cause the stent to expand radially. Likewise, retracting the device proximally may not be optimal either, because application of force in a proximal direction on the distal end of the stent also can axially compress the stent, and can cause the stent to expand radially.

The deployment techniques fall into two categories, one is where the members are deployed outside the stent to pull or push accordingly depending on distal or proximal placement, or sometimes both. See, U.S. Pat. Nos. 6,123,723, 6,280,465, and US Publication No. 2011/0307049. Other techniques deploy the members inside of the stent. See, US Publication No. 2014/0277360, and U.S. Pat. Nos. 5,702,418, and 6,955,685. However, self-expanding device delivery systems with multiple members pose two problems:

1) After the physician has deployed the self-expanding device, he/she must re-sheathe the delivery wire back into the microcatheter, to then dispose of the wire. When recapturing the delivery wire, the members of the delivery system can get caught on the deployed device, and can subsequently alter the position of the device in the anatomy. The more members on the wire, the more often this can happen.

2) The more members on the delivery wire, the more difficult it is to manufacture. In order to build the delivery system, a manufacturer can either secure polymer/metal sleeves onto a core wire, or grind down a core wire to create members on a wire. The more members on a delivery wire, the more material must be used to add and secure members, or, the more the grind profile has to change to accommodate all of the members.

Thus, would be desirable to provide a delivery system for expandable stents that offers the flexibility of engaging the device and for pushing and/or pulling the device proximally or distally as desired. Also desirable is a simplified manufacturing method.

SUMMARY

The dual function delivery system described below reduces these two problems by combining certain members into one. This invention provides a unique advantage of a delivery system that includes one feature that can perform two functions.

Thus, a self-expanding element delivery apparatus can include a catheter having an inner lumen, a self-expanding element, and a delivery wire disposed within and extending through the inner lumen and the self-expanding element. The self-expanding element has a proximal end, a distal end, an intermediate portion between the proximal and distal ends, and a proximal and distal anchor member disposed accordingly. The element is configured to have a compressed configuration dimensioned to fit within the inner lumen of the catheter, and an expanded configuration dimensioned larger than the catheter. The self-expanding element is in the compressed configuration when disposed within the inner lumen, and is in the expanded configuration when disposed outside the inner lumen. The delivery wire also has a proximal and distal portions, an intermediate portion located between, a dual function bump member disposed approximate to the intermediate portion of the delivery wire, and a pusher bump member disposed approximate to the proximal portion of the delivery wire. There can be a bump member distance between the dual function bump member and the pusher bump member so that only one of the dual function bump member and the pusher bump member can contact one of distal anchor member and the proximal anchor member.

In another example, the delivery wire is moveable within the inner lumen and the self-expanding element, and the dual function bump member and the pusher bump member are configured to engage at least one of the proximal and distal anchor members when the delivery wire is translated longitudinally. Also a force applied longitudinally to the delivery wire is transmitted through at least one of the bump members to at least one of the anchor members to move the self-expanding element through the catheter when the self-expanding element is in the compressed configuration within the catheter.

Further, when the delivery wire is moved distally, the dual function bump member contacts the distal anchor member and the pusher bump member does not contact the proximal anchor member during an initial deployment phase. Then, when the delivery wire is moved distally and the distal end of the self-expanding element is outside the catheter and expanded and the proximal end of the self-expanding element is still in the compressed configuration, the pusher bump member contacts the proximal anchor member and the dual function bump member does not contact the distal and the proximal anchor members during a final deployment phase. After the final deployment phase, the self-expanding element is in the expanded configuration.

An example of a recapture phase can occur when the distal end of the self-expanding element is outside the catheter and expanded and the proximal end of the self-expanding element is still in the compressed configuration. When the delivery wire is moved proximally the dual function bump member contacts the proximal anchor member and the pusher bump member does not contact the proximal anchor member during. Also, after the recapture phase, the self-expanding element is in the compressed configuration inside the catheter.

An example of a method of deploying a self-expanding element with a catheter, delivery wire and the self-expanding element including distal and proximal anchor members thereon, the steps include disposing a dual function bump member on the delivery wire between the proximal and distal anchors and disposing a pusher bump member outside of the self expanding element proximal of the proximal anchor. To deploy the self-expanding element, a user distally moves the delivery wire and engages the dual function bump member to the distal anchor member and unengages the pusher bump member. Next, the pusher bump member can be engaged to the proximal anchor member and disengaging the dual function bump member, thus, fully deploying the self-expanding element. As used in the example herein, "unengaging" connotes that in the first instance when the dual function bump is engaged, the pusher bump is not engaged with the proximal anchors and never engages with the distal anchors. Also, that the when the dual function bump is engaged, the pusher bump is not engaged either during deployment or recapture.

Another example to recover a partially deployed self-expanding element has the steps of proximally moving the delivery wire and engaging the dual function bump member to the proximal anchor member and disengaging the pusher bump member.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention. The drawing figures depict one or more implementations in accord with the present teachings, by way of example only, not by way of limitation.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Figure 1:
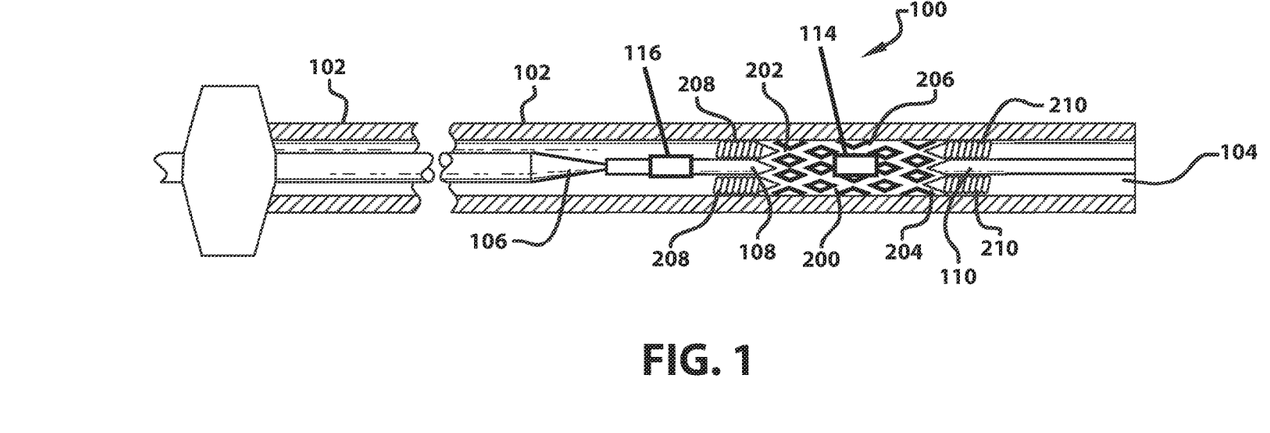
FIG. 1 is an enlarged partial cross-sectional view of an apparatus for delivering and releasing a self-expanding element to a treatment site in a patient's body lumen, according to an example of the invention.
Figure 2:
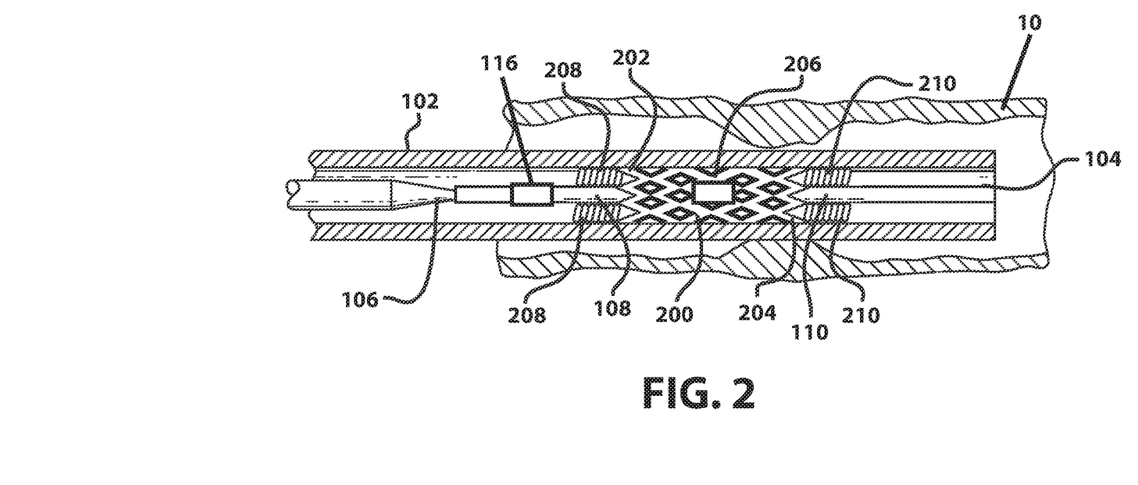
FIG. 2 is an enlarged partial cross-section view of the system apparatus within the body lumen and the self-expanding element in the compressed configuration.
Figure 3:
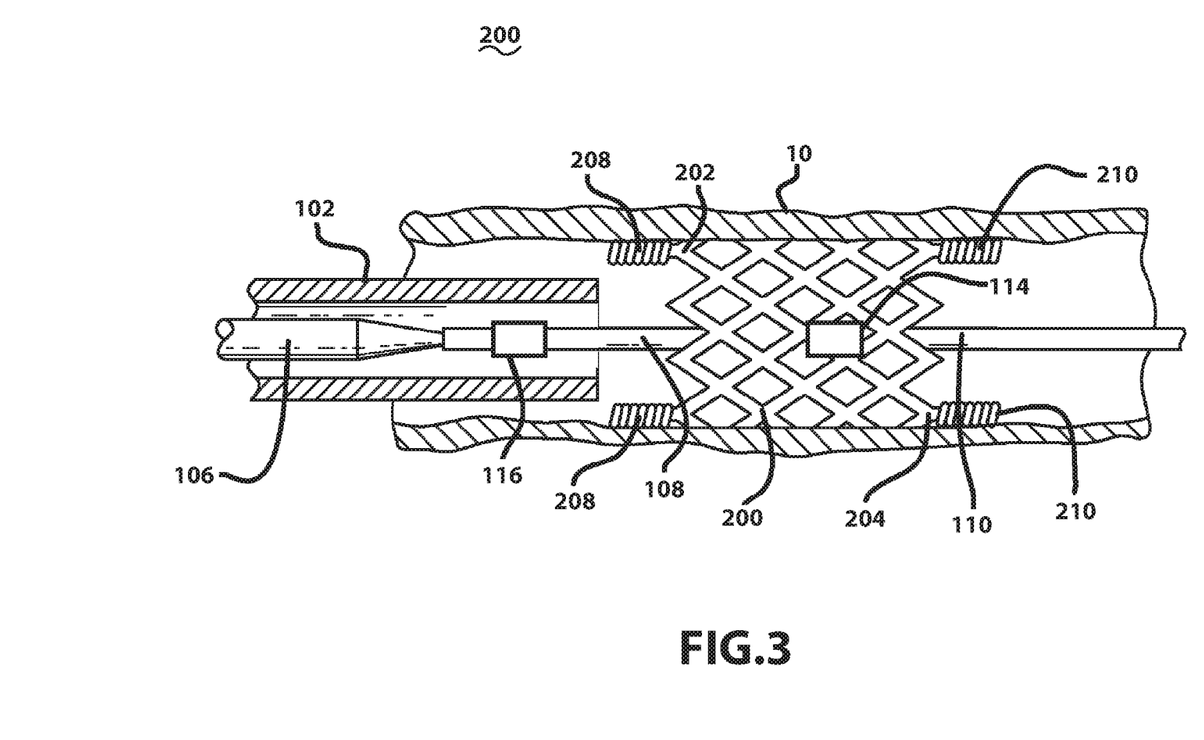
FIG. 3 is a cross-section view illustrating an expanded configuration of the self-expanding element within the patient's body lumen.
Figure 4:
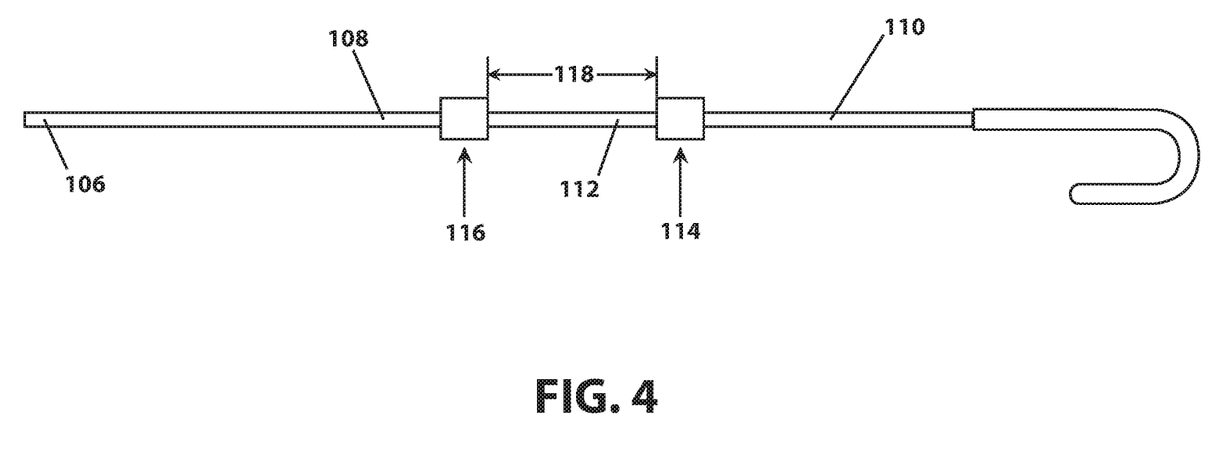
FIG. 4 is a section of the delivery wire with the dual function bump member and pusher bump member.
Figure 5:
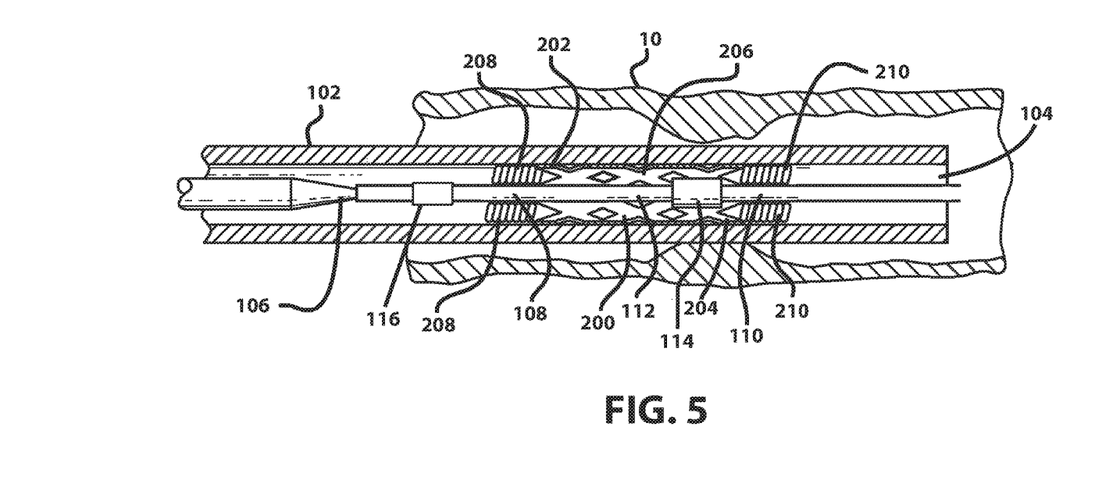
FIG. 5 is an enlarged partial cross-section view, similar to FIG. 2, with a portion of the self-expanding element cut away to expose the bump members on the delivery wire.

Examples of the present invention provide for an apparatus 100 that can deliver and release a self-expanding element 200 to a treatment site in a patient's body lumen (e.g. vasculature) 10. As is illustrated in FIG. 1-3, the apparatus 100 includes a catheter 102 having an inner lumen 104, the self-expanding element 200 can have an inner space (not illustrated), a proximal end 202, a distal end 204, and an intermediate section 206 located between the ends 202, 204. Typically, the self-expanding element 200 has a compressed configuration and an expanded configuration. In the compressed configuration, as illustrated in FIGS. 1 and 2, the self-expanding element 200 can be dimensioned to fit within the inner lumen 104 of the catheter 102. The catheter 102 can aid in constraining the self-expanding element 200 so it does not expand when contained within the catheter 102. Other elements can be used to constrain the self-expanding element 200 as are known in the art.

In the expanded configuration, as illustrated in FIG. 3, the self-expanding element 200 expands to fit the dimensions of the patient's body lumen 10. The expanded dimension of the self-expanding element 200 allows the apparatus 100 to pass therethrough, to either advance to a second location or be withdrawn. The self-expanding element 200 can be expandable under its inherent proprieties, based at least on its original shape and the nature of the materials that make up the element. Examples of the self-expanding element 200 can be one of pear shaped, ovoid, and elliptical when at its expanded diameter. The construction of the self-expanding element 200 is known to those of skill in the art.

The self-expanding element 200 can also include one or more anchor members 208, 210, such as proximal anchor members 208 at the proximal end 202 of the self-expanding element 200, and distal anchor members 210 disposed at the distal end 204 of the self-expanding element 200. The anchor members 208, 210 may be projections which extend generally parallel to a longitudinal axis of the self-expanding element 200 and extend downward toward the longitudinal axis of the self-expanding element 200. The anchor members 208, 210 can serves as a radiopaque marker for improved visualization during the deployment of the self-expanding element 200 within the body lumen 10. The anchor members 208, 210 can be used to align the self-expanding element 200 so it can be pushed and pulled through the catheter 102 without damage or deformation.

FIGS. 4-8 illustrate that the apparatus 100 can also include the delivery wire 106 disposed within and extending through the lumen 104 of the catheter 102. The delivery wire 106 has a proximal portion 108, a distal portion 110, and an intermediate portion 112 located between the proximal and distal portions 108, 110 of the delivery wire 106. The delivery wire 106 can have a dual function bump member 114 and a pusher bump member 116 extending radially outwardly from the delivery wire 106 and configured to engage the anchor members 208, 210 when the delivery wire 106 is translated longitudinally toward the one or more anchor members 208, 210. Force applied longitudinally to the delivery wire 106 can be transmitted through one or both of the bump members 114, 116 to the one or more anchor members 208, 210 to the self-expanding element 200. This acts to move the self-expanding element 200 through the catheter 102 when the self-expanding element 200 is constrained within the catheter 102. This is explained in more detail below.

As illustrated, the dual function bump member 114 is disposed between the proximal and distal anchor members 208, 210, toward the intermediate section 206 of the self-expanding element 200 and/or the intermediate portion 112 of the delivery wire 106. This places the dual function bump member 114 "inside" the self-expanding element 200. The pusher bump member 116 on the other hand, is disposed on the proximal portion 108 of the delivery wire 106, proximal to the proximal anchor members 208 of the self-expanding element 200. This places the pusher bump member 116 "behind" the self-expanding element 200. This placement facilitates both the deployment and retrieval of the self-expanding element 200 from the catheter 102 into the body lumen 10.

Figure 6:
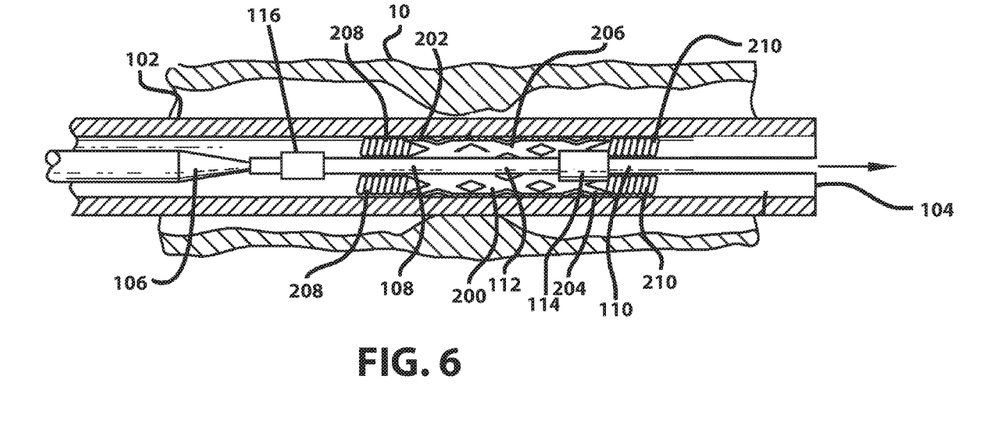
FIG. 6 is an enlarged partial cross-sectional view illustrating the initial deployment phase and pushing the self-expanding element distally.

Turning first to deployment, FIG. 6 illustrates the initial deployment phase. Here, as the delivery wire 106 is moved distally, the dual function bump member 114 contacts the distal anchor members 210 of the self-expanding element 200. In this phase, the dual function bump member 114 is pushing the self-expanding element 200 from the "inside." The pusher bump member 116 is not in contact with the proximal anchor members 208 during this phase. By having only the dual function bump member 114 pushing during the initial deployment phase there is reduced localized buckling and/or radial expansion of the self-expanding element 200. This reduces the force needed to drive the self-expanding element 200 distally out of the catheter 102.

Figure 7:
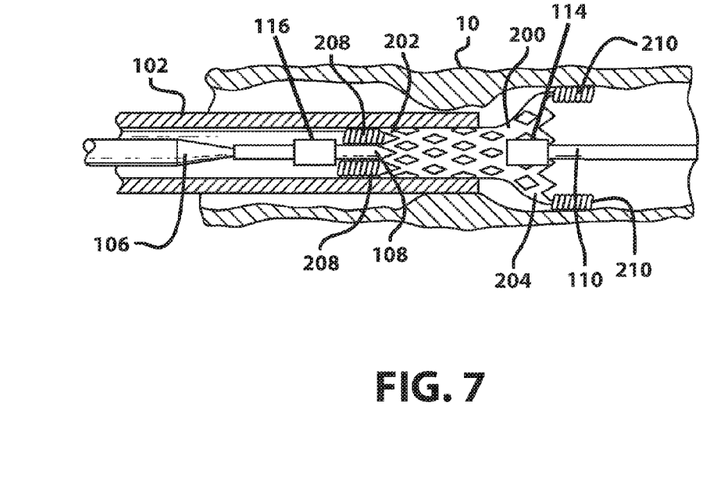
FIG. 7 is an enlarged partial sectional view of final deployment phase where the self-expanding element is moved distally with a proximal portion of the self-expanding stent compressed within a deployment catheter and a distal portion of the self-expanding stent expanded within the patient's body lumen.

In the final deployment phase, as illustrated in FIG. 7, the self-expanding element 200 is partially outside of the catheter 102 and partially expanded. The distal end 204 is expanded, while the proximal end 202 remains compressed. In the expanded state, the distal anchor members 210 have expanded away from both the delivery wire 106 and the dual function bump member 114. Now, the dual function bump member 114 no longer contacts the self-expanding element 200 and cannot apply distal or "forward" force to the self-expanding element 200. To deploy the remainder of the self-expanding element 200, the delivery wire 106 is advanced until the pusher bump member 116 contacts the proximal anchor members 208. The pusher bump member 116 is able to contact the proximal end 202 of the self-expanding element 200 since that section is still compressed inside the catheter 102. The pusher bump member 116 is "outside" of the self-expanding element 200 and pushes the remainder of the self-expanding element 200 completely outside the catheter 102. This allows the self-expanding element 200 to fully expand and be positioned inside the body lumen 10. Once fully expanded, the self-expanding element 200 has a larger diameter than the delivery wire 106, the bump members 114, 116 and the catheter 102, allowing this portion of the apparatus 100 to pass therethrough and be removed. This full deployment is illustrated in FIG. 3.

Given the above, the dual function bump member 114 and the pusher bump member 116 have a bump member distance 118 therebetween. The bump member distance 118 can be calibrated based on the size of the self-expanding element 200. The bump member distance 118 needs to be such that only one of the bump members 114, 116 contacts the anchor members 208, 210 at a given time when the delivery wire 106 is being moved either proximally or distally. Said another way, when the dual function bump member 114 contacts one set of the anchor members 208, 210, the pusher bump member 116 is not in contact with the proximal anchor members 208. Then, when the pusher bump member 116 is in contact with the proximal anchor members 208, the dual function bump member 114 is not in contact with either the distal anchor members 110 or the proximal anchor members 208. Another example of the bump member distance 118 is that it must be greater than a distance from the proximal piece of the distal anchor member 210 and the proximal piece of the proximal anchor member 208.

Figure 8:
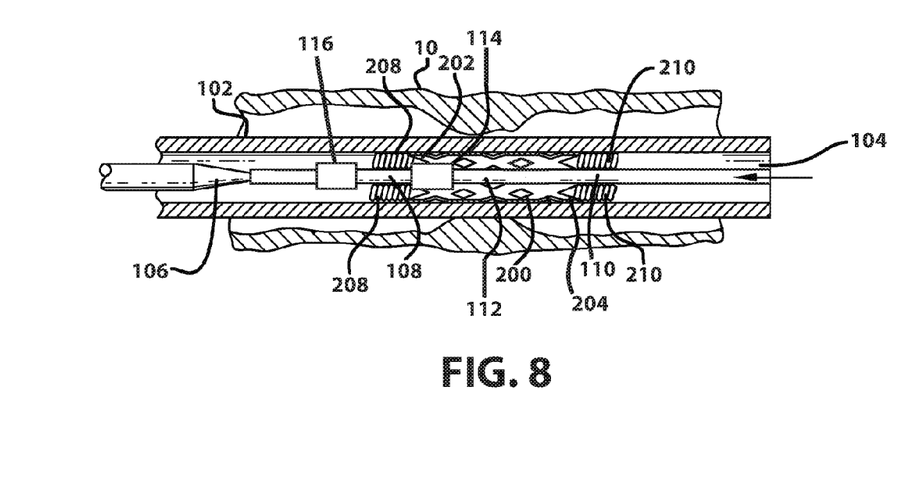
FIG. 8 is an enlarged partial cross-sectional view illustrating the recapture phase of pulling the self-expanding element proximally into the catheter.

In some instances, the self-expanding element 200 needs to be recaptured before full deployment. Once reason for recapture can be that the self-expanding element 200 needs to be better placed within the body lumen 10. FIG. 8 illustrates the recapture phase. Here, the self-expanding element 200 is pulled back/recaptured into the catheter 102 when the delivery wire 106 is pulled proximally. The dual function bump member 114 now moves proximally away from the distal anchor members 210 to engage the proximal anchor members 208. This engagement now pushes the proximal anchor members 208 proximally and forces the self-expanding element 200 to compress back into the catheter 102 until it is again fully enclosed in the inner lumen 104 of the catheter 102. During the recapture phase, the pusher bump member 116 does not contact the proximal anchor members 208 or the self-expanding element 200.

Figure 9:
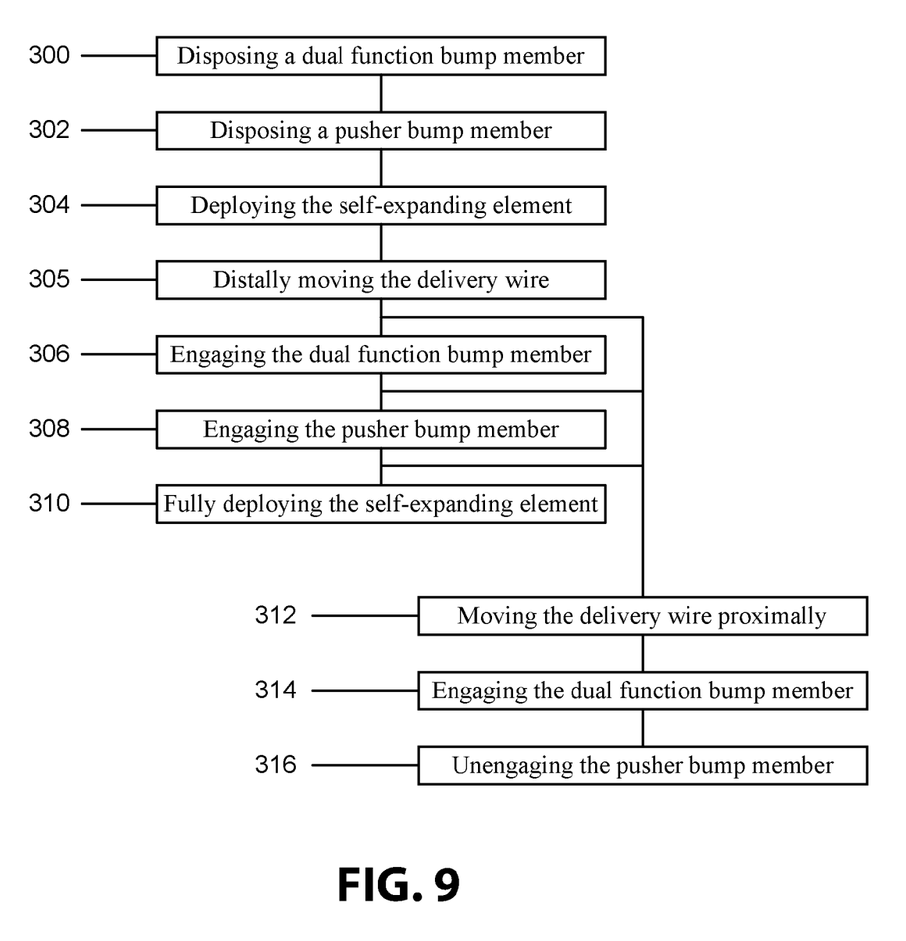
FIG. 9 is a flow diagram illustrating an example of a method of using the apparatus of the present invention.

FIG. 9 illustrates an example of the method of the present invention. In an apparatus 100 as described above, a dual function bump member 114 can be disposed between proximal and distal anchors 208, 210 of a self expanding element 200 (step 300). A pusher bump member 116 can be disposed outside of the self expanding element 200 on the proximal side (step 302). The self-expanding element 200 can be deployed (step 304) by distally moving the delivery wire 106 (step 305) till engaging the dual function bump member 114 to the distal anchor members 210 while the pusher bump member 116 remains unengaged (step 306). Next, the dual function bump member 114 is disengaged when the pusher bump member 116 engages the proximal anchor members 208 of the self-expanding element 200 (step 308). Finally, the self-expanding element 200 is fully deployed and the apparatus 100 can be removed (step 310).

In a recapture method example, any time before full deployment, the self-expanding element 200 can be recovered into the catheter 102. This includes the step of moving the delivery wire 106 proximally (step 312) to engage the dual function bump member 114 to the proximal anchor member 208 (step 314) while the pusher bump member 116 is unengaged (step 316).

Note that certain features of the apparatus 100 can be formed from materials that have a shape memory structure. For example, a metal alloy such as nickel titanium (NiTi), also known as Nitinol. Other elements may be formed of a non-superelastic material, such as spring steel or MP35N, an alloy of 35% nickel, 35% cobalt, 20% chromium, and 10% molybdenum, by weight. Features may be laser cut from the material, secure onto the delivery wire, or the delivery wire can be grinded down to create the above described elements.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A method of deploying a self-expanding element including a catheter with a delivery wire and the self-expanding element including distal and proximal anchor members thereon, the steps comprising:

disposing only a dual function bump member on the delivery wire between the proximal and distal anchors;

disposing a pusher bump member outside of the self expanding element proximal of the proximal anchor;

deploying the self-expanding element, comprising the steps of:

distally moving the delivery wire;

engaging the dual function bump member to the distal anchor member and the pusher bump member is unengaged to the proximal anchor member; and engaging the pusher bump member to the proximal anchor member and disengaging the dual function bump member; and recovering a partially deployed self-expanding element comprising the steps of:

proximally moving the delivery wire; and engaging the dual function bump member to the proximal anchor member and disengaging the pusher bump member.

2. The method of claim 1, further comprising the step of fully deploying the self-expanding element.

* * * * *